US00PP16714P3

(12) United States Plant Patent
Miyazaki

(10) Patent No.: US PP16,714 P3
(45) Date of Patent: Jun. 27, 2006

(54) ***SENECIO* PLANT NAMED 'SUNSENEBAPIBA'**

(50) Latin Name: ***Senecio cruentus*×*Senecio heritieri***
Varietal Denomination: Sunsenebapiba

(75) Inventor: Kiyoshi Miyazaki, Hikone (JP)

(73) Assignee: Suntory Flowers Limited, Tokyo (JP)

( * ) Notice: Subject to any disclaimer, the term of this patent is extended or adjusted under 35 U.S.C. 154(b) by 96 days.

(21) Appl. No.: 10/815,189

(22) Filed: Mar. 31, 2004

(65) Prior Publication Data

US 2005/0223454 P1 Oct. 6, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,122 P2 10/2001 Miyazaki

FOREIGN PATENT DOCUMENTS

JP PBR 10503 9/2002

OTHER PUBLICATIONS http://www.yourdictionary.com. "capitula".*
http://glossary.gardenweb.com "capitulum".*
Explanation of Application documents and family documents thereof.
Suntory Flowers Ltd., "Flower & Green, autumn and winter catalog 2004" Published 2003 (with Explanation for IDS Document).
Moerheim New Plant bv, "Suntory Collection 2004" Published 2003 (with Explanation for IDS Document).
Sakata seed Co., Japan, "The Catalog for Gardening Farm, 94' autumn—'95 spring, Sakata's flowering plants, nursery stock, and bulb, No. 70" Published 1994 (with Explanation for IDS Document).
The Royal Horticultural Society, England, "The Plant Finder, 1994/95 Edition" Published 1994 (with Explanation for IDS Document).

* cited by examiner

*Primary Examiner*—Kent Bell
*Assistant Examiner*—Louanne Krawczewicz Myers
(74) *Attorney, Agent, or Firm*—Christie, Parker and Hale, LLP

(57) ABSTRACT

Disclosed herein is a new variety of *Senecio* plant having a semi-dwarf, obconical shaped with abundant branching and small leaves. The capitula are single and medium size, the ray florets having strong reddish purple with white center coloration. The blooming time is early and flowering duration is longer than *Senecio cruentus*. 'Sunsenebapiba' has low fertility.

2 Drawing Sheets

Botanical/commercial classification: *Senecio cruentus*× *Senecio heritieri*.
Varietal denomination: Sunsenebapiba.

BACKGROUND OF THE VARIETY

The present invention relates to a new variety of *Senecio* plant, which originated from the crossing of the cultivar 'Extra Rose White' as the female parent with a variety of *Senecio heritieri* as the male parent.

There are many varieties of *Senecio L.* and *Senecio cruentus* cultivated in the world. Many cultivated *Senecio* varieties have capitula of a single color of white, pink red, blue or violet, while others have marginal variegation with off color parts.

The female parent 'Extra Rose White' (unpatented) is a cultivar of *Senecio cruentus*. It is an early flowering variety having dwarf and mounding shape with large leaves. It has small single capitula, the ray florets having vivid purplish red with white center coloration. The seed of 'Extra Rose White' is commercially available.

The male parent *Senecio heritieri* is a cultivar having a high and dome-shaped growth habit with abundant branching and small leaves. It has small single capitula, the ray florets having strong purple with vague white center coloration. *Senecio heritieri* was introduced from nurseries in England, and, to Applicant's knowledge has no variety name, and is neither patented nor sold in the United States.

In January 1996, 'Extra Rose White' as the female parent was crossed with *Senecio heritieri* as the male parent, in Hakushu-cho, Kitakoma-gun, Yamanashi-ken, Japan. The seedlings obtained from that crossing were grown in pots in glasshouses and evaluated in July 1996. One seedling was selected in December 1996, in view of its growth habit, flower color and flowering time. That seedling was propagated by cutting and trialed in pots starting in July 1999, at Hakushu-cho, Kitakoma-gun, Yamanashi-ken, Japan. The botanical characteristics of that plant were then examined, using similar varieties 'Sunsenereba' (U.S. Plant Pat. No. 12,122) and 'Rouge Chigasaki' (unpatented) for comparison. As a result, it was concluded that this *Senecio* plant is distinguishable from any other variety, whose existence is known to us, and is uniform and stable in its characteristics. The new variety of *Senecio* plant was named 'Sunsenebapiba'.

In the following description, the color-coding is in accordance with the Horticultural Colour Chart of The Royal Horticultural Society, London, England (R.H.S.).

SUMMARY OF THE VARIETY

This new variety is unlike any *Senecio* commercially available known to the inventor as evidenced by the following unique combinations of characteristics.

1. Semi-dwarf, obconical plant shape having abundant branching with small leaves.
2. The capitula are single and medium size. The ray florets having strong reddish purple (near R.H.S. 78B) with white center coloration. The disc floret color is deep reddish purple (near R.H.S. 79B.)
3. Blooming time is early, and flowering duration is long.
4. The new variety has low fertility.

The new variety 'Sunsenebapiba' differs from the similar variety 'Sunsenereba' in the following points.

1. The plant size of 'Sunsenebapiba' is more compact than that of 'Sunsenereba'.
2. The capitulum diameter of 'Sunsenebapiba' is smaller than that of 'Sunsenereba'.
3. The peduncle length of 'Sunsenebapiba' is shorter than that of 'Sunsenereba'.
4. The blooming time of 'Sunsenebapiba' is earlier than that of 'Sunsenereba'.

The new variety 'Sunsenebapiba' differs from the similar variety 'Rouge Chigasaki' in the following points.

1. The plant size of 'Sunsenebapiba' is larger than that of 'Rouge Chigasaki'.
2. The branches of 'Sunsenebapiba' are more numerous than those of 'Rouge Chigasaki'.
3. The leaf of 'Sunsenebapiba' is smaller than that of 'Rouge Chigasaki'.
4. The ray floret color of 'Sunsenebapiba' is strong reddish purple (near R.H.S. 78B) with white center coloration and the disc floret color is deep redddish purple (near R.H.S. 79B). The ray floret color of 'Rouge Chigasaki' has deep red (near R.H.S. 60B) with white center coloration and the disk color is deep purplish red (near R.H.S. 61A).
5. The blooming time of 'Sunsenebapiba' is earlier than that of 'Rouge Chigasaki'.
6. The flowering duration of 'Sunsenebapiba' is longer than that of 'Rouge Chigasaki'.

This new variety of *Senecio* Plant 'Sunsenebapiba' was asexually reproduced by the use of cuttings at Hakushu-cho, Kitakoma-gun, Yamanashi-ken, Japan, and homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during January 2003 while growing outdoors in 12 cm pots at an age of approximately 5 months at Yokaichi-shi, Shiga-ken, Japan.

DESCRIPTION OF THE VARIETY

Figure 1:
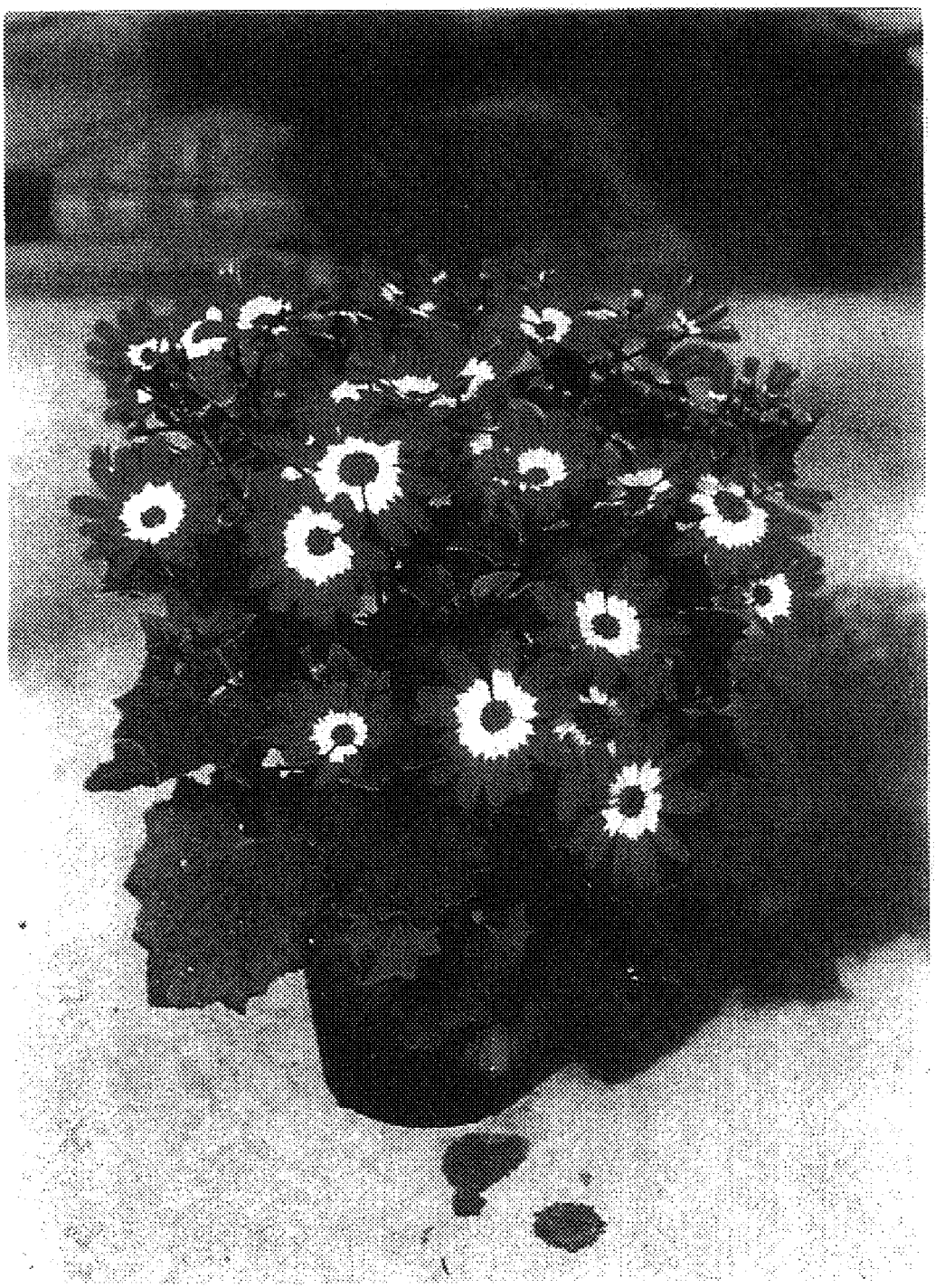
FIG. 1 illustrates a typical plant of the new variety of *Senecio* plant 'Sunsenebapiba', growing in a pot.
Figure 2:
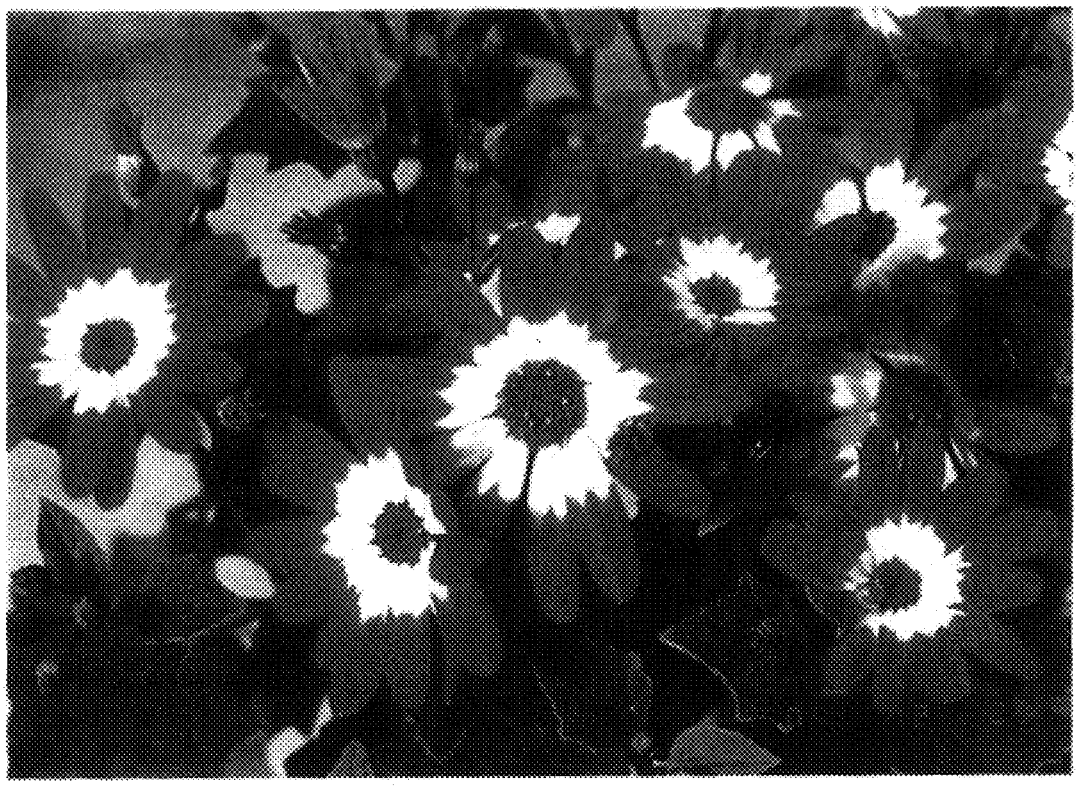
FIG. 2 illustrates a close-up view of capitula of the new variety of *Senecio* plant 'Sunsenebapiba'.

The botanical characteristics of the new and distinct variety of *Senecio* plant named 'Sunsenebapiba' are as follows, when observed during January at Yokaichi-shi, Shiga-ken, Japan, at an age of approximately 5 months.

Plant:

*Growth habit.*—Semi-dwarf, obconical.
*Height.*—Approximately 27.5 cm.
*Width.*—Approximately 21.0 cm.

Stem:

*Length.*—Approximately 18 cm.
*Thickness.*—Approximately 4.4 mm.
*Color.*—Near R.H.S. 144A (strong yellow green).
*Anthocyanin coloration.*—Absent.
*Number of branches.*—Abundant.
*Type of primary lateral shoot.*—Branch from every node.
*Pubescence.*—Moderate.
*Length of internode.*—Approximately 1.8 cm.

Leaf:

*Whole shape.*—Cordate.
*Leaf margin.*—Dentate, weakly undulated.
*Apex shape.*—Acute.
*Base shape.*—Cordate.
*Length.*—Approximately 8.5 cm.
*Width.*—Approximately 9.4 cm.
*Diameter of petiole.*—Approximately 3.2 mm.
*Length of petiole.*—Approximately 6.2 cm.
*Color of petiole.*—Near R.H.S. 144B.
*Color of upper surface.*—Near R.H.S. 146B.
*Color of lower surface.*—Near R.H.S. 138B.
*Anthocyanin coloration of reverse surface.*—Absent.
*Pubescence of upper surface.*—Moderate.
*Pubescence of lower surface.*—Dense.
*Pattern of venation.*—Reticulate venation.
*Color of venation.*—Near R.H.S. 135B.
*Stipule.*—Absent.

Inflorescence cluster (gathering of corymbs):

*Shape of inflorescence cluster.*—Flat.
*Diameter of inflorescence cluster.*—Approximately 29 cm.
*Height of inflorescence cluster.*—Approximately 16 cm.

Capitulum:

*Transected shape of capitulum.*—Flat.
*Diameter of capitulum.*—Approximately 5.7 cm.
*Disc diameter.*—Approximately 1.0 cm.
*Color of ray floret.*—Upper surface near R.H.S. 78B; lower surface near R.H.S. N78C.
*Marginal variegation.*—Present. The white center coloration is approximately 2.4 cm in diameter.
*Ray floret length.*—Approximately 2.4 cm.
*Ray floret width.*—Approximately 0.8 cm.
*Shape of ray floret.*—Oblong.
*Lengthwise warp of ray floret.*—Flat.
*Shape of ray floret tip.*—Obtuse.
*Shape of ray floret base.*—Obtuse.
*Margin of ray floret.*—Entire, apex is bitten.
*Texture.*—Velvety.

Disc floret:

*Shape.*—Tubular, trumpet shape.
*Color (both surfaces).*—Near R.H.S. N79B to N78A.
*Length.*—Approximately 8.5 mm.
*Diameter.*—Approximately 1.0 mm.
*Margin.*—5 lobed, star shape.
*Apex shape.*—Acute.
*Base shape.*—Fused.
*Number of ray florets.*—13.
*Number of disc florets.*—Approximately 95.
*Diameter of pedicel.*—Approximately 1.3 cm.
*Length of pedicel.*—Approximately 2.7 cm.
*Color of pedicel.*—Near R.H.S. 138A, Near R.H.S. N79B at distal end.
*Number of capitula per plant.*—Abundant.
*Scent.*—Present.

Bud:

*Hardiness.*—Tolerant to 0° C. However, the plant would be seriously damaged by frost, the same as other *Senecio* plants, at any temperature.

*Length.*—Approximately 5.5 mm.

*Diameter.*—Approximately 6.0 mm.

*Shape.*—Globose.

*Surface.*—Smooth.

*Color.*—Near R.H.S. 138A.

Involucre:

*Type.*—Bracts in a whorl, fused at the base, not recurved.

*Length of bracts* (*separated portion*).—Approximately 3.0 mm.

*Width of bracts* (*separated portion*).—Approximately 1.0 mm.

*Apex shape of bracts.*—Acute.

*Margin of bracts.*—Entire.

*Number of bracts.*—Approximately 14.

*Color* (*both sides*).—Near R.H.S. 144A.

*Anthocyanin coloration.*—Absent.

Pistil:

*Color.*—Near R.H.S. 80A (vivid reddish purple).

*Number.*—1 per ray and disc floret.

*Type.*—Style branches truncate.

Stamen:

*Pollen.*—Moderate, color near R.H.S. 10A.

*Color.*—Near R.H.S. 77A (deep reddish purple).

*Type.*—Synantherous. A disc floret has 5 connate anthers with separated filament. Ray floret has no stamen.

*Blooming time.*—Beginning of November (cutting in July). Plants start flowering about 5 months after planting root cuttings in Japan.

*The lastingness of an individual bloom on the plant.*—Approximately 2 weeks at around 15° C.

Hardiness:

*Cold.*—Good.

*Heat.*—Good.

Resistance:

*Disease.*—Good.

*Insect.*—Good.

The new variety and *Senecio cruentus* have similar resistance to powdery mildew, leaf spot, aphid, whitefly and thrips. The new variety, 'Sunsenebapiba' is most suitable for flower potting.

It is claimed:

1. A new variety of *Senecio* plant named 'Sunsenebapiba', substantially as herein illustrated and described.

* * * * *